United States Patent
Matson et al.

(10) Patent No.: US 10,024,842 B2
(45) Date of Patent: Jul. 17, 2018

(54) METHODS AND DEVICES FOR QUANTITATING BLOOD SAMPLES

(71) Applicant: IXCELA, INC., Bedford, MA (US)

(72) Inventors: Samantha A. Matson, Groton, MA (US); Beena E. Thomas, Malden, MA (US); Swati Bhasin, Acton, MA (US)

(73) Assignee: IXCELA, INC., Bedford, MA (US)

(*) Notice: Subject to any disclaimer, the term of this patent is extended or adjusted under 35 U.S.C. 154(b) by 218 days.

(21) Appl. No.: 15/143,174

(22) Filed: Apr. 29, 2016

(65) Prior Publication Data

US 2016/0320367 A1 Nov. 3, 2016

Related U.S. Application Data

(60) Provisional application No. 62/154,520, filed on Apr. 29, 2015.

(51) Int. Cl.
| | |
|---|---|
| *G06K 9/00* | (2006.01) |
| *G01N 33/49* | (2006.01) |
| *B01L 3/00* | (2006.01) |
| *G01F 22/00* | (2006.01) |

(52) U.S. Cl.
CPC ............ *G01N 33/49* (2013.01); *B01L 3/5023* (2013.01); *G01F 22/00* (2013.01); *B01L 2200/143* (2013.01); *B01L 2300/021* (2013.01)

(58) Field of Classification Search
CPC . G01N 33/49; B01L 3/5023; B01L 2200/143; B01L 2300/021; G01F 22/00
See application file for complete search history.

(56) References Cited

U.S. PATENT DOCUMENTS

| | | | | |
|---|---|---|---|---|
| 6,006,119 | A * | 12/1999 | Soller | A61B 5/14535 356/39 |
| 6,255,061 | B1 | 7/2001 | Mori et al. | 435/14 |
| 8,748,176 | B2 * | 6/2014 | Monuki | A61K 35/30 435/354 |
| 8,748,186 | B2 * | 6/2014 | Kendall | G01N 1/2813 382/184 |

(Continued)

FOREIGN PATENT DOCUMENTS

WO  WO2013016038  1/2013 ............ G01N 15/14

OTHER PUBLICATIONS

El-Hajjar, Dana F., et al. "Validation of use of annular once-punched filter paper bloodspot samples for repeat lead testing." Clinica chimica acta 377.1-2 (2007): 179-184.*

(Continued)

*Primary Examiner* — Jonathan S Lee
(74) *Attorney, Agent, or Firm* — Hayes Soloway P.C.

(57) ABSTRACT

Methods and devices for analyzing blood sample volumes are provided. In particular, the disclosure provides a method for estimating the volume of a blood sample on a substrate including the steps of acquiring an image of the blood sample. A coverage or area of the blood sample may be obtained from the image and compared to a standard curve to obtain a volume estimate of the blood sample. The disclosure also proves a device for scanning one or more blood samples on a substrate. The device includes three layers that may be assembled to hold multiple samples between the layers. The device also includes labels and may be disassembled for decontamination and reloading of samples.

18 Claims, 15 Drawing Sheets

(56) References Cited

U.S. PATENT DOCUMENTS

| | | | | |
|---|---|---|---|---|
| 9,903,798 | B1* | 2/2018 | Astle | G01N 1/312 |
| 2004/0028875 | A1 | 2/2004 | Van Rijn et al. | 428/98 |
| 2004/0151637 | A1 | 8/2004 | Davin | 422/102 |
| 2007/0227967 | A1 | 10/2007 | Sakaino et al. | 210/502.1 |
| 2008/0102535 | A1 | 5/2008 | Chase et al. | 436/173 |
| 2009/0298191 | A1* | 12/2009 | Whitesides | G01N 33/523 |
| | | | | 436/164 |
| 2011/0115905 | A1 | 5/2011 | Beumer et al. | 348/135 |
| 2012/0028342 | A1* | 2/2012 | Ismagilov | B01L 3/502738 |
| | | | | 435/283.1 |
| 2012/0309636 | A1 | 12/2012 | Gibbons et al. | 506/9 |
| 2013/0011042 | A1 | 1/2013 | Satish et al. | 382/134 |
| 2013/0301901 | A1 | 11/2013 | Satish et al. | 382/134 |
| 2014/0368822 | A1* | 12/2014 | Morrison | G01N 21/59 |
| | | | | 356/432 |
| 2016/0089669 | A1* | 3/2016 | Regnier | B01L 3/502 |
| | | | | 435/309.1 |

OTHER PUBLICATIONS

International Search Report and Written Opinion issued in application No. PCT/US16/30226, dated Oct. 7, 2016 (12 pgs).
International Preliminary Report on Patentability issued in application No. PCT/US16/30226, dated Nov. 9, 2017 (8 pgs).

* cited by examiner

METHODS AND DEVICES FOR QUANTITATING BLOOD SAMPLES

CROSS REFERENCE TO RELATED APPLICATIONS

This application claims priority from U.S. Provisional Application Ser. No. 62/154,520, filed Apr. 29, 2015, the contents of which are incorporated herein by reference.

FIELD

The present disclosure relates generally to methods and devices for blood sampling, and more particularly to methods and devices for estimating blood sample volumes. More specifically, the disclosure relates to a method for estimating the volume of blood samples collected on a filter or other substrate. The disclosure also more specifically relates to a device that may be used for holding filters and other substrates for scanning images of the dried blood samples that will be used for quantitating the collected blood.

BACKGROUND

Blood samples are routinely taken in clinics, hospitals or specialized labs by trained professional for diagnostic purposes. A more cost effective and less invasive alternative to traditional venipuncture method is collecting blood by finger stick on a filter paper. The blood is then dried and sample known as dried blood spot (DBS) can be stored or processed as required. The DBS can then be used for analysis of various small molecules, metabolites, proteins etc. DBS is a powerful blood sampling procedure as it allows collection of blood at any time or place. No special training is required to collect the blood and the blood can be stored or shipped at ambient temperature for a period of time.

One major drawback associated with DBS is the difficulty in quantitating the analytes as the volume of blood loaded cannot be ascertained when directly loaded onto the filter paper in non-lab settings. Volumetric application of blood is not practical when collecting samples in the field. A number of factors influence the spread of blood on a substrate like filter paper. The hematocrit of blood greatly influences the spread of blood on the filter paper (higher hematocrit blood spreads less compared to low hematocrit blood). Also there is differential spread of the blood due to capillary effect (blood spreads more on thinner paper compared to thicker paper). Finally, the chromatographic effect results in uneven distribution of blood components (some blood components may move faster than others). So, one area of the DBS may have different composition than another area. Therefore, the often used practice of punching out specific sizes of blood spots may not be as accurate as processing the whole blood sample entirely collected on the filter.

Different methods have been proposed to overcome the difficulty in quantitating the analytes from DBS. One method proposes quantitating amount of endogenous potassium levels to calculate the hematocrit of loaded blood. While this method reports accurate estimation of hematocrit, it requires additional processing and analysis of blood samples and filter paper. Another method uses diffuse reflection to estimate the hematocrit of blood in the DBS to allow for sample volume correction. While accurate, this method requires additional expensive lab equipment, sample processing and specialized software to analyze the DBS.

Accordingly, there exists an urgent need in the relevant field for a technique that provides accurate estimation of blood volume. Such techniques should be capable of being performed in a cost effective manner, as the whole purpose of DBS technology is to reduce the expenses associated with blood collection, storage and shipment. Such techniques should also allow for estimation of the blood volume in the entire spot, so that analytes can be quantitated accurately.

Furthermore, current devices known in the art used to scan blood samples, including dried blood spots on filter paper, suffer from problems such as high risk of contamination of samples, difficulty in keeping multiple samples organized, isolating samples from human exposure, and limited ability to quickly, efficiently and consistently process multiple samples or batches of samples. Accordingly, there also exists a need in the relevant field for devices that overcome these limitations of the prior art, including devices that may be used in conjunction with the novel techniques disclosed herein.

SUMMARY

Embodiments of the present disclosure provide methods and devices for processing blood samples. In particular, the present disclosure provides novel methods of estimating the volume of blood samples collected on filters and other substrates in a consistent and accurate manner. This is essential for quantifying analytes in blood samples collected in different settings, including non-laboratory settings. The methods disclosed herein address the major technical problem of quantification associated with an otherwise powerful blood sampling method that allows collection, storage and transport of blood in the field in a minimally invasive and cost-effective manner.

Accordingly, in one embodiment, the disclosure provides a method for estimating the volume of blood samples comprising the following steps: obtaining a sample of blood (e.g., by sticking a finger with lancet to get blood sample); spotting the blood sample on a substrate; obtaining an image of the blood sample; determining an approximate coverage or area of the image of the sample; and comparing the determined approximate coverage or area to a standard curve to determine an estimated volume of the blood sample.

In one embodiment determining the approximate coverage or area of the image of the sample comprises calculating a coverage ratio of the blood sample on the substrate, wherein calculating the coverage ratio of the blood sample on the substrate preferably comprises counting pixels in the image of the blood sample.

In another embodiment calculating the coverage ratio of the blood sample on the substrate comprises counting pixels in an image of a blank substrate, wherein calculating the coverage ratio of the blood sample on the substrate preferably comprises determining a ratio of the number of pixels counted in the image of the blood sample to the number of pixels counted in the image of the blank substrate.

In one embodiment the standard curve comprises data from two or more blood samples of known volumes plotted against data of approximate coverages or areas of the two or more blood samples determined from images of the two or more blood samples. In such embodiment the two or more blood samples of known volumes preferably comprise samples with varying hematocrits.

In another embodiment the image of the sample of blood is obtained with a scanner or a camera.

In yet another embodiment the substrate comprises a filter comprising paper.

The present disclosure also provides devices for holding blood samples collected on filter or other substrates. The devices provide the benefits of ease of use, simplified and more efficient decontamination, reduction of mistakes when handling samples due to human error, the ability to easily log samples and keep records of samples, and increased durability over previous devices. With respect specifically to scanning of samples, the devices provide the advantages of the ability to fit virtually any known scanner or similar imaging device, the ability to allow for uniform and consistent sample spacing and scanning distance, and ease of cross-comparison between different samples. Thus, the devices can provide the ability to perform more efficient and accurate scanning in a reduced amount of time over previously known devices.

Accordingly, in one embodiment, the disclosure provides a device for scanning filters (dried blood samples) comprising: a first layer comprising one or more transparent portions; a second layer comprising one or more holes, wherein said one or more holes are formed through the second layer and are sized to each receive a dried blood sample filter; and a third layer comprising one or more raised portions; wherein said one or more transparent portions of the first layer overlap with the one or more holes of the second layer and the one or more raised portions of the third layer when the first, second and third layers are aligned and stacked on top of each other with the second layer between the first and third layers.

In one embodiment each of the one or more raised portions of the third layer fits into each of the one or more holes in the second layer. In such embodiment the raised portions of the third layer preferably are sized to compress a dried blood spot filter against the first layer and within a hole of the second layer when the first, second and third layers are aligned and stack on top of each other with the second layer between the first and third layers. In one embodiment the first, second and third layers are configured to be securely assembled to one another such that the second layer is positioned between the first and third layers. In such embodiment the first, second, and third layers preferably are secured by an attachment mechanism selected from the group consisting of one or more screws, one or more bolts, one or more nails, a chemical adhesive, a tape, one or more elastic bands, and combinations thereof.

In one embodiment at least one of the first, second or third layers comprises plexiglass.

In one embodiment the first, second and third layers are substantially rectangular in shape and substantially the same size.

In one embodiment the first layer is entirely transparent.

In one embodiment the one or more raised portions on the third layer comprise acrylic discs.

In one embodiment the device further comprises one or more labels for identifying the dried blood sample filters. In such embodiment the labels preferably comprise one or more codes comprising one or more of letters, words, numbers, colors, bar codes, and matrix bar codes, and/or are removable.

In yet another embodiment the one or more holes in the second layer are uniformly sized and/or uniformly spaced apart from one another.

The features, functions, and advantages that have been discussed can be achieved independently in various embodiments of the present disclosure or may be combined in yet other embodiments, further details of which can be seen with reference to the following description and drawings.

Other features, functions and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

In the following description, reference is made to the accompanying drawings, which form a part hereof, and in which is shown, by way of illustration, various embodiments of the present disclosure. It is understood that other embodiments may be utilized and changes may be made without departing from the scope of the present disclosure.

Method for Estimating Volume of Blood Sample

In a preferred embodiment, the methods provided herein may be used to estimate the volume of blood in a dried blood spot on a paper filter or other substrate. While not wishing to be bound by theory, it is believed that blood spread on filters primarily is influenced by the capillary effect (i.e., the spread is inversely proportional to the thickness of the paper), chromatographic effect (i.e., how fast or slow the blood components spread through the filter) and the hematocrit (i.e., high hematocrit blood spreads less and vice versa). In a preferred embodiment, the HemaForm™ filter (Spot On Sciences, Inc.) was selected because its unique design allows spread of blood evenly and the filter paper thickness is consistent. It is believed that this results in more consistent blood sampling as a result of reduced hematocrit and chromatographic effects. The results obtained were reproducible and consistent with these filters; however, this technology may be applied to other types of filters too.

Figure 1:
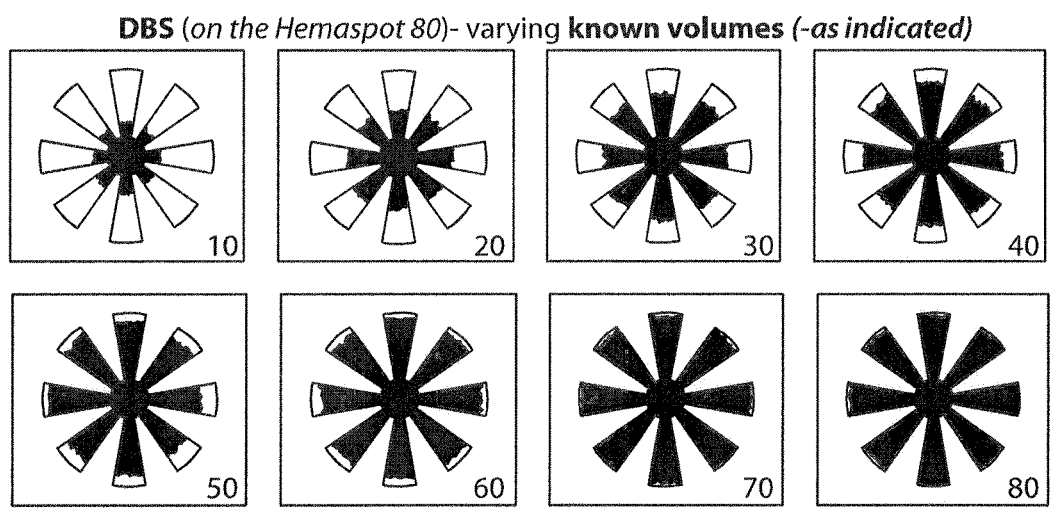
FIG. 1 shows blood spots of specific known volumes on filter paper.

The present disclosure is based, in part, on the hypothesis that the spread of the blood on the filter would be proportional to the volume of blood being spotted. We can exploit this property to measure the volume of blood. First, specific incremental volumes of fresh blood were spotted on different HemaForm™ filters and visually analyzed after overnight drying. FIG. 1 depicts eight different HemaForm filters with varying known volumes of blood spotted on the filters. Specifically, the known volumes of blood spotted increase from left to right, top to bottom in the images in FIG. 1. Thus, a quick visual inspection of the spotted filters reveals that the spread of the blood on the filter is proportional to the volume of the blood spotted on it. As this confirmed the correctness of the hypothesis, the next step was to actually measure the spread of blood. Since there are no methods currently available to correlate the spread to the volume of blood in a dried blood spot, it therefore became necessary to develop a novel analytical tool that would enable the spread to be quantitated.

Our method allows consistent and accurate estimation of blood volume loaded onto a substrate (e.g., filter paper), which is essential for quantifying analytes in blood samples collected in non-lab settings. This method addresses a major technical problem of quantification associated with an otherwise powerful blood sampling method that allows collection, storage and transport of blood in the field in a minimally invasive and cost-effective manner.

Figure 2:
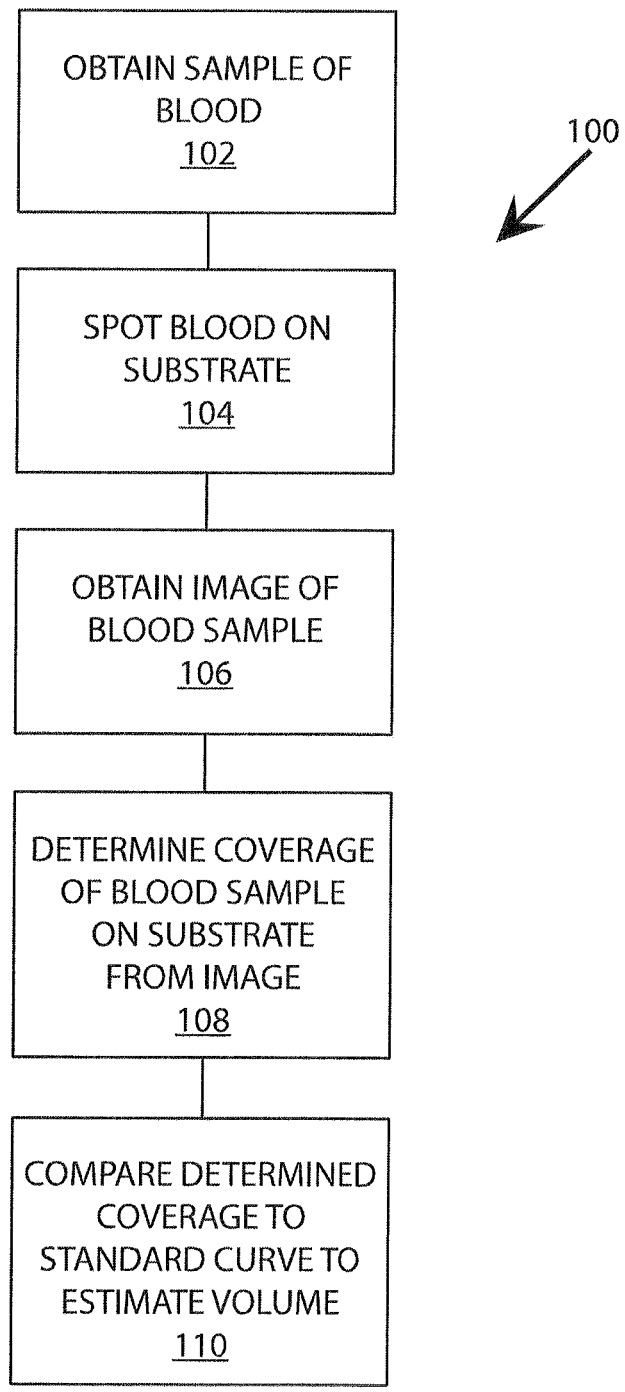
FIG. 2 shows a flow diagram of an exemplary embodiment of a method for estimating blood volume disclosed herein.

FIG. 2 is a flow chart of an exemplary embodiment of the present invention, wherein a method 100 is provided for estimating the volume of a blood sample. It should be noted that any process descriptions or blocks in flow charts should be understood as representing modules, segments, portions of code, or steps that include one or more instructions for implementing specific logical functions in the process, and alternate implementations are included within the scope of the present disclosure in which functions may be executed out of order from that shown or discussed, including substantially concurrently or in reverse order, depending on the functionality involved, as would be understood by those reasonably skilled in the art of the present disclosure.

As is shown in block 102 of FIG. 2, a sample of blood is obtained from a human or animal patient by any method known in the art. This may include traditional venipuncture, wherein blood is obtained directly from a patient's vein. The blood may also be collected via a finger prick or via a "prick" of any other part of the patient's body. Blood collected via this method is typically obtained from blood capillaries near the surface of the skin by piercing the skin with a lancet or similar device. The blood from the "finger prick" may be collected into a capillary tube and then dispensed onto a filter or directly spotted onto the filter paper.

As is shown in block 104 of FIG. 2, the sample of blood obtained or a portion of the sample of blood obtained is spotted or otherwise placed onto a substrate. The substrate may be any material known in the art that is capable of retaining a sample of blood. In a preferred embodiment, a paper filter may be used as the substrate. Paper filters, including Guthrie cards, HemaForm filters and others, are well known in the art for their use in dried blood spot sampling. In certain embodiments, the substrate may be a composite material and/or may be coated, for example, with silica.

In block 106 of FIG. 2, an image is obtained of the spotted blood sample. The image may be obtained with any imaging device known in the art, preferably after the blood has dried completely. Thus, a camera, a scanner, or other similar imaging devices may be used successfully with the disclosed methods. Selection of an appropriate imaging device may include such considerations as ease of use, the need for a fixed platform for acquiring multiple images, the ability to process multiple filters, image quality, and the ability to control and managing various imaging settings and controls.

In one embodiment, a camera may be used to obtain the image. Typically, the camera will be mounted on a tripod or other device to hold it steady and to obtain images that are consistent and reproducible. In an alternative embodiment, a scanner may be used to obtain the image. For example, an HP Photosmart 1300 or other similar device may be used to obtain the image. For any imaging device used, it may be beneficial to adjust the resolution of the acquired image to a preferred or standardized resolution. For example, a resolution of 600 dpi may be used. Resolution may also be controlled and adjusted via software, as is discussed below. The image obtained may be provided in a digital format such that it may be viewed on a computing or other electronic device. This further allows the image to be viewed with image editing or image analysis software.

In block 108 of FIG. 2, an approximate coverage or area of the blood sample on the substrate is determined from the image of the blood sample. For purposes of this disclosure, the coverage of the blood sample may be measured or estimated in terms of absolute area or, alternatively, as a ratio of areas, such as percent coverage. In a preferred embodiment, the determination of the coverage may be performed by counting pixels in the image. This is preferably done with the use of image analysis or image editing software. Numerous software programs for this purpose are known in the art (e.g., GIMP2, Adobe Photoshop).

Prior to obtaining a pixel count, various settings of the software may need to be adjusted to obtain an optimal image for counting the pixels. For example, it may be beneficial to adjust the resolution of the images. Using a fixed resolution across all images may help to ensure accurate results. Further optimization can be carried out by choosing the right threshold for pixel selection with the GIMP2 image analysis program. A lower threshold may often lead to non-specific selection, whereas a higher threshold may interfere with color selection of pixels.

Figure 3:
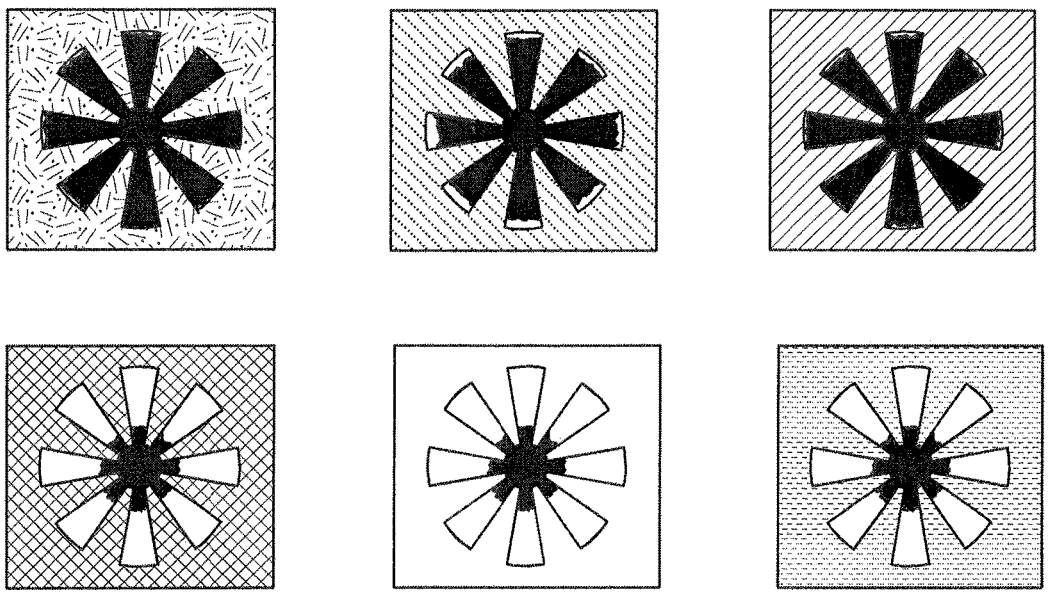
FIG. 3 shows images of blood spots obtained using a variety of backgrounds.

It may also be beneficial to optimize resolution in order to minimize the shadow interference in the images. Shadows observed along peripheries of the substrate (e.g., shadows along the "petals" of the HemaForm™ filter) may interfere with pixel selection during pixel analysis and counting. Alternatively, or in addition to adjusting settings in the scanning software for this purpose, a variety of backgrounds may be used in the images in order to minimize these effects, as is shown in FIG. 3.

The software may be utilized to count only those pixels that correspond to the portion of the image that actually depicts the blood spot. Thus, any pixel that covers or at least partially overlaps with a blood spot may be counted. Alternative methodologies for determining whether an individual pixel should be counted may be used, so long as the methodology is consistent with respect to other images or data to which the image may be compared. In certain embodiments, the absolute number of pixels that correspond to the blood spot may be used to determine the area of the blood spot. The pixels representing the blank areas of the filter (i.e., the portions of the filter to which the blood has not spread) may also be counted. From this additional count, a total number of pixels may be acquired for use in the area or coverage calculation or, by adding to the pixels counted in the blood spot and comparing to a known number of pixels corresponding to an entire blank filter, to ensure accurate and precise pixel counting.

In alternative embodiments, a "percent coverage" area may be determined, for example, by additionally counting the pixels representing a blank substrate (e.g., filter) in an image of the blank substrate. It is important that the image of the blank substrate be acquired with the same settings (e.g., resolution) as the image of the blood spot for accurate and meaningful comparison of the two images. To obtain a percent coverage calculation, a ratio of the number of pixels counted in the blood spot to the number of pixels counted in the blank filter is determined.

As is shown in block 110 of FIG. 2, the coverage or area of the blood spot determined in block 108 may be compared to a standard curve, table, chart or other data to calculate the volume of the blood spot. Such a standard curve, table, chart or other data may include data on blood samples with known volumes. For example, a series of blood samples of different known volumes may be spotted separately on substrates. Images of each of the spotted blood samples may be obtained, along with area or percent coverage calculations obtained from the images. These calculated areas or percent coverages may then be plotted against or otherwise compared to the known volumes to obtain a standard curve, table, chart, etc. A best-fit line may be used to assist with comparing the data. For any subsequently obtained blood samples, an estimation of the volume of the blood sample may be determined by comparing the area of percent coverage of the blood sample to the standard curve or other data generated in block 110. It may further be necessary to update the data in the standard curve as necessary to ensure its accuracy. Moreover, it may be desirable that the known samples used to generate the standard curve vary in other characteristics, for example, hematocrit, to correct for possible effects of such characteristics on the spreading area of the blood sample on the substrate.

Example 1: Generation of a Standard Curve

Figure 4:
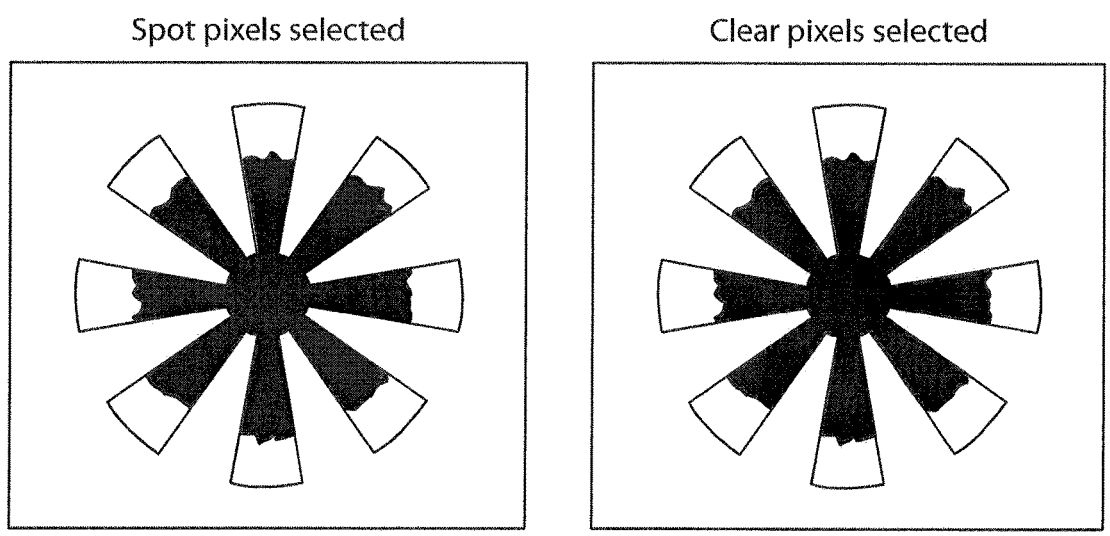
FIG. 4 shows two images of a dried blood spot with the spot pixels selected in one image and the surrounding clear pixels selected in the other image.

A standard curve may be generated by the following exemplary method. A series of exact known volumes of fresh blood were spotted onto HemaForm™ filters and dried overnight. For imaging, a camera was fixed onto a tripod. The camera settings were adjusted for optimum resolution, and all of the images were then taken keeping the settings fixed. Pixels were counted using the image analysis program GIMP2. This software is an ideal choice because it is freely available from the internet and it has proven successful in carrying out analyses (though other image analysis programs like Adobe Photoshop etc. may work equally well). For reference, an image of a blank HemaForm™ filter was acquired, and the total number of pixels corresponding to the blank filter was determined from the image. The pixels in the dried blood spot and the surrounding empty (clear) region of the filter around the blood spot were also selected and counted, as is shown in FIG. 4.

Figure 5:
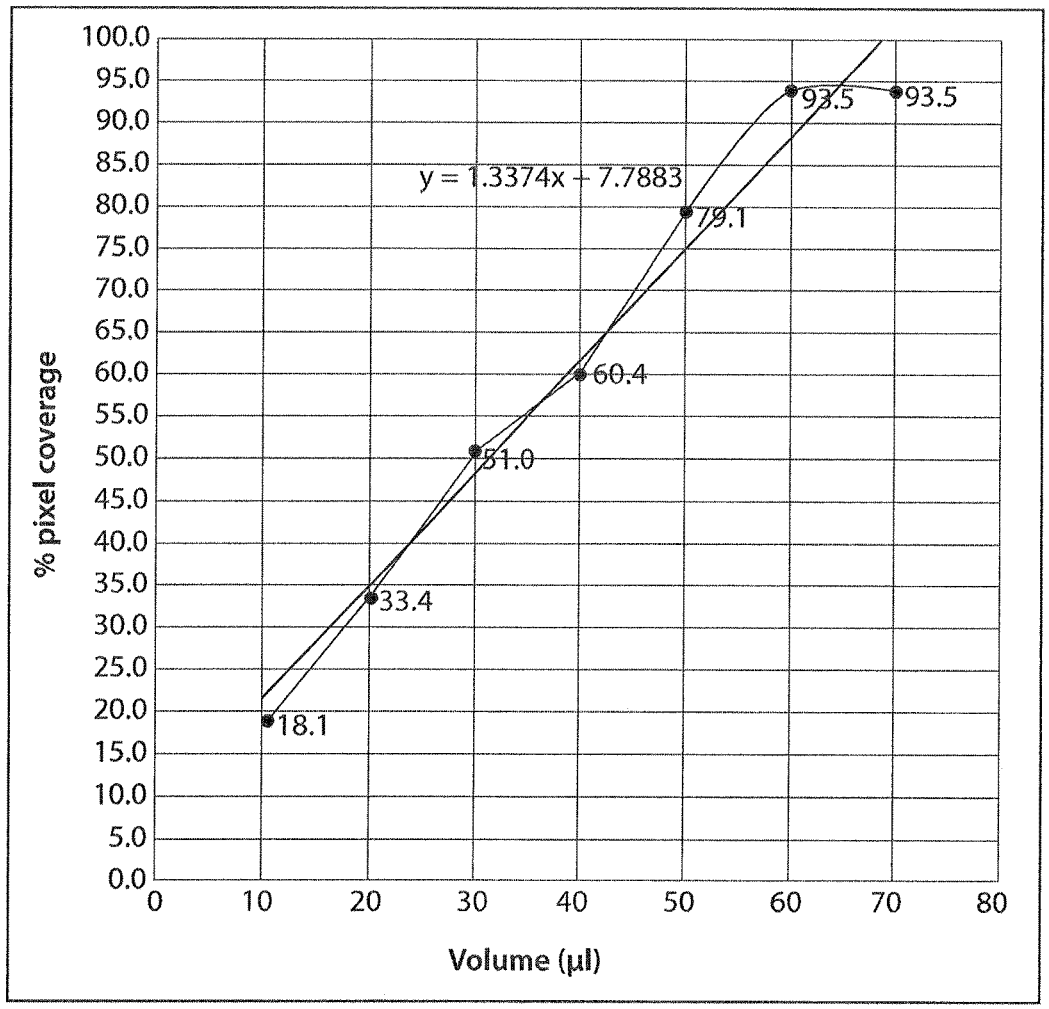
FIG. 5 shows an exemplary graph of pixel coverage versus blood spot volume.

Next, the pixel coverage was determined by dividing the pixels in the spot by the total pixels in the blank filter. FIG. 5 shows the results of the pixel covered vs. volume of blood spotted. The slope of a best-fit line fitted to the data points was determined, as is also shown in FIG. 5. To test the accuracy of the line in FIG. 5, estimations of the blood sample volumes obtained from the slope of the line were then compared to actual known volumes. Our volume estimations were within 1-5 µl of the actual volumes spotted, thereby demonstrating the efficacy of the method. However, with additional refinements to the analysis, even greater accuracy may be achieved.

Example 2: Generation of a Combined Standard Curve

A combined standard curve may be obtained by the following exemplary method. A scanner (e.g., HP Photosmart 3100) was selected based on the considerations mentioned above. Image resolution was also optimized with the GIMP2 image analysis program to improve the quality of pixel analysis and counting.

Figure 6:
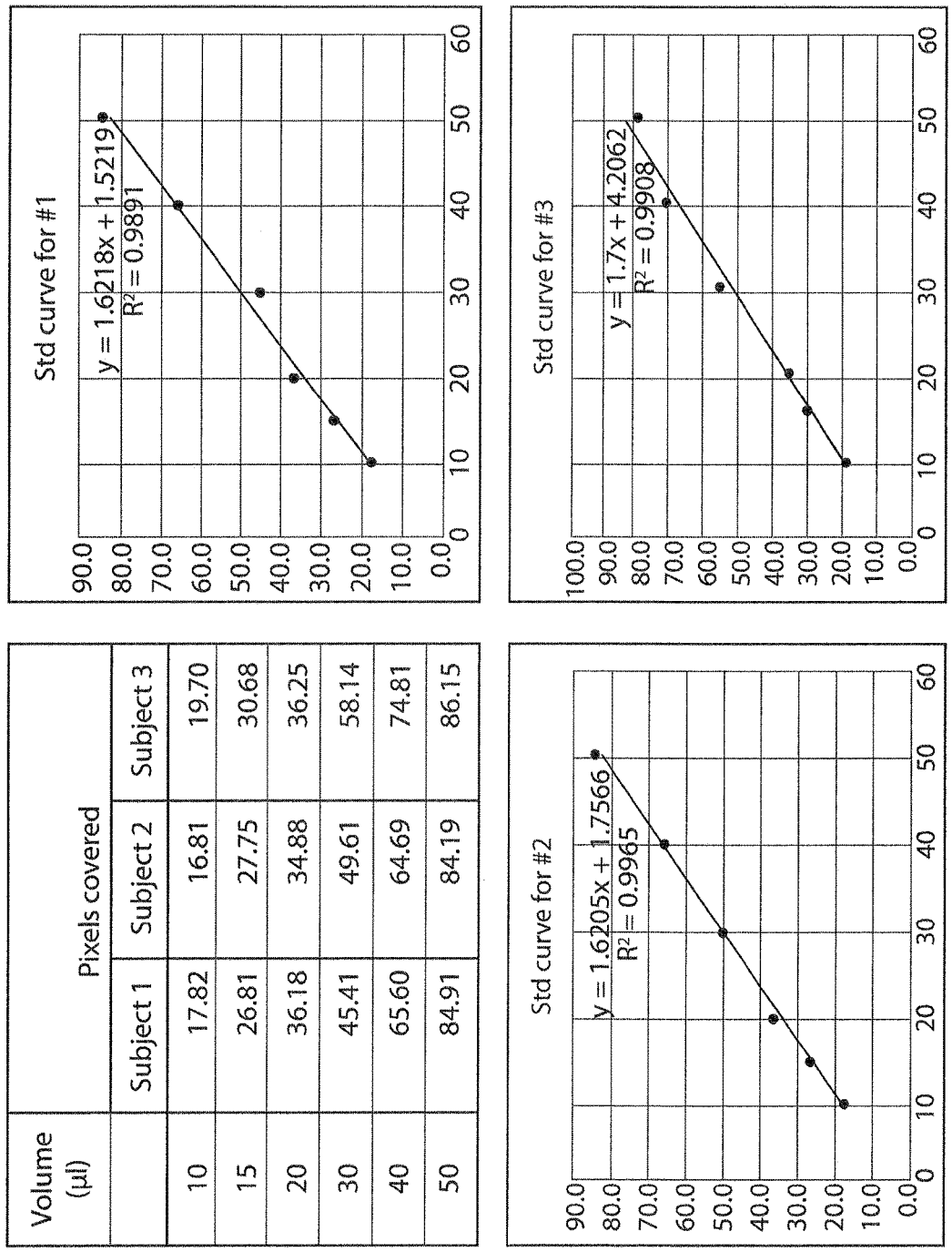
FIG. 6 shows exemplary data and corresponding standard curves of pixel coverage versus blood volume generated for blood samples from three different subjects.
Figure 7:
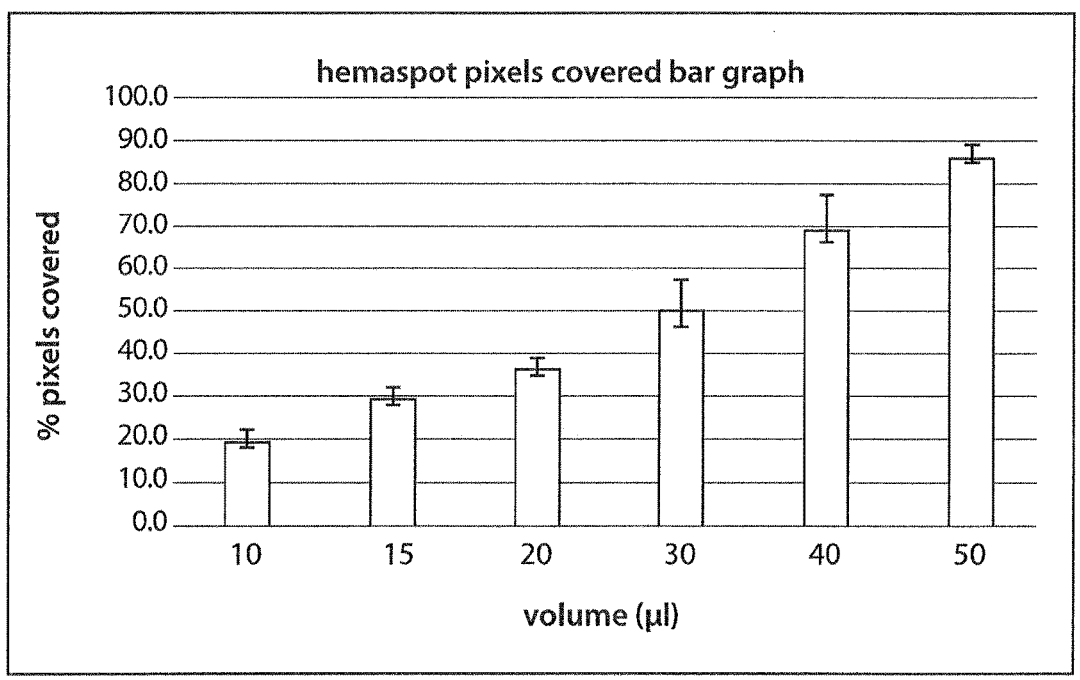
FIG. 7 shows an exemplary bar graph of pixel coverage versus blood volume generated from the combined results of blood samples from three different subjects.
Figure 8:
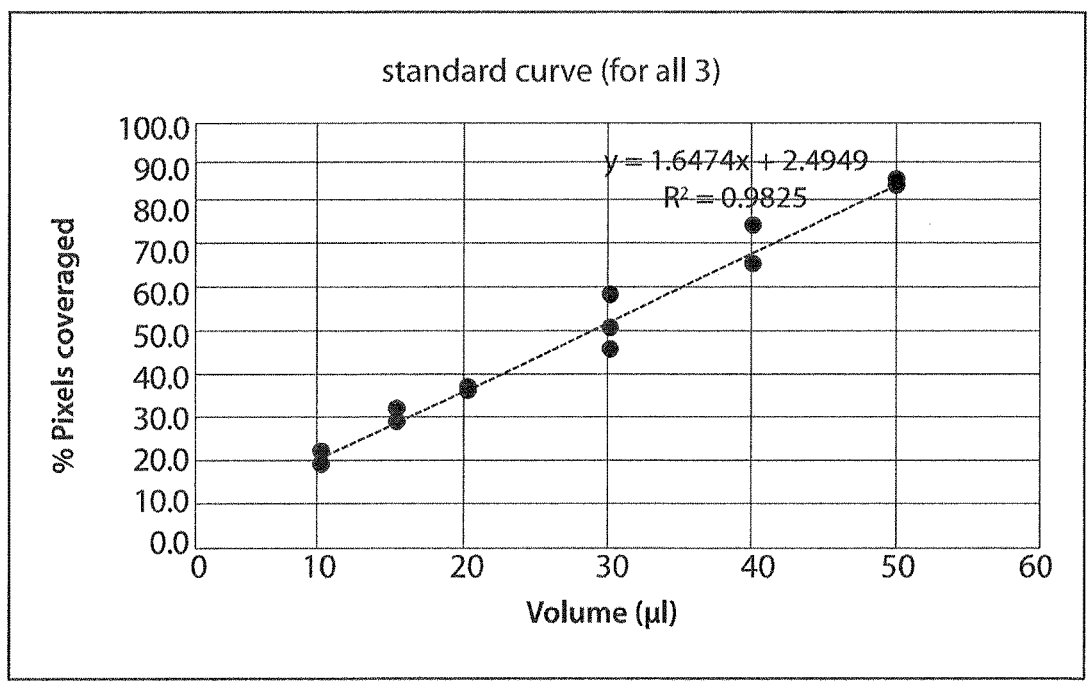
FIG. 8 shows an exemplary standard curve of pixel coverage versus blood volume generated from the combined results of blood samples from three different subjects.

Bloods from three different individuals varying in age, gender and hematocrit was analyzed to account for the differences in the spread of blood. Fresh blood from the three subjects was spotted on filters at known different volumes. Images of these spotted blood samples were acquired and used to calculate the pixels covered. From this data, three separate standard curves were generated, as is shown in FIGS. 6 and 7. A combined standard curve, shown in FIG. 8, was also generated from which the slope was determined. The combined curve was used to determine the volumes of unknown samples.

Prediction accuracy when using the methods disclosed herein is quite high, and estimated volumes may generally fall within 2-3 µl or less of the actual volumes. Hematocrit was found to have an effect on the obtained measurements. Thus, for very low and very high hematocrit levels, the calculated volume may generally fall within 5% the actual volume spotted. Blood lower in hematocrit may tend to spread further because there is a greater amount of plasma in a given volume. Conversely, a higher hematocrit blood may typically spread less due to a lower amount of plasma in a given sample size. Thus, measurements obtained using the disclosed methods may directly correlate with the volume of plasma in the blood. Further, metabolite levels measured from whole blood provides a more accurate measure of disease state or progression and also allow for a more consistent comparison with plasma.

Validation of the accuracy of the standard curve may be accomplished by spotting known volumes on the filter. Blinded analyses are typically performed in these cases, such that the volumes are not known to the person carrying out the volume analysis. Table-1 shows a sample of some volumes that were analyzed by blinded analysis. As can be seen from Table 1, all estimated volumes fall within 0.2-3.5 µl of the actual known volumes.

TABLE 1

| Subject | Calculated volume using image analysis (µl) | Actual volume loaded on filter (µl) |
| --- | --- | --- |
| 1 | 8.64 | 9.00 |
| 2 | 11.3 | 10.00 |
| 3 | 19.26 | 20.00 |
| 4 | 18.89 | 20.00 |
| 5 | 36.5 | 33.00 |
| 6 | 43.06 | 40.00 |
| 7 | 43.1 | 40.00 |
| 8 | 48.46 | 50.00 |
| 9 | 49.80 | 50.00 |
| 10 | 52.11 | 50.00 |

Example 3: Method for Estimation of Blood Volume

In a preferred embodiment, estimation of blood volume may be performed as follows. This technique is based on calculating the pixels in the DBS image. The volume of blood in the spot is measured by comparing its pixels-against-pixel count to a standard curve of DBS of known volumes. The step by step procedure is described below:

Step 1: Pixel Calculation (a) Scanning DBS

To count the pixels in a DBS, the first step is to scan the DBS. DBS samples are scanned along with a blank filter (on which blood has not been spotted) on the scanner. The scanning resolution is set to a fixed setting—this can be any setting but once chosen, should be kept same for all analyses. For example, a resolution of 600 DPI may be used.

(b) Image Analysis Using GIMP 2 Image Analysis Software

This software is available for free download from the internet. The scanned DBS is cropped using the selection tool and the pixels are separately counted for the exact blood spot area and the blank area. Pixels are also counted for a blank filter likewise.

(c) Actual Pixel Coverage

Percent pixels in the spot are calculated by determining the ratio of pixels in the spot to the overall pixels in the blank filter.

Step 2: Preparation of the Standard Curve

Collect blood from different individuals (ideally with a varying hematocrit) in heparin/EDTA tubes. The freshly collected blood is then spotted in exact known volumes ranging from 5 to 60 µl individually (in triplicate samples) to prepare DBS of known volumes. These are left to dry overnight followed by scanning as described in (1) above. The pixel coverage is calculated and the standard curve is created for the pixel coverage against the volume. The slope is determined for the standard curve.

Step 3: Calculation of Blood Volume in the DBS

Pixel coverage is calculated for a DBS of unknown volume as described in step (1) above and the volume is calculated on the basis of the slope determined as discussed in step (2).

Plate Reader Device

The devices disclosed herein may be used for holding filters on which blood samples have been collected (e.g., DBS). In a preferred embodiment, this disclosure provides a device for scanning or imaging multiple blood samples quickly and without cross-contamination and with minimal scanning-related shadow artifacts. The device also provides the benefits of keeping samples organized, holding them securely in place for scanning, and isolating the sample from human exposure as much as possible. Additional advantages of the device include that it may fit virtually any scanner, is easy to use, and is durable. Because it may keep sample space and scanning distances uniform, it will allow for cross-comparison of samples scanned from one batch to the next. This may greatly reduce time spent trying to get samples scanned exactly the same way or having to adjust algorithms to calculate volumes and other characteristics of blood samples. The device is made of separate components that may be assembled for scanning and disassembled for decontamination and sample preparation. The device may also assist in logging and identification of samples as it can keep a record of which samples have been scanned via an incorporated label template.

In another embodiment, the present disclosure provides a device for scanning dried blood spots on a filter that may be utilized with all methods disclosed herein. In a preferred embodiment, the device enables scanning of multiple dried blood spots simultaneously. As is depicted in FIGS. 9-15, the device may include up to four parts that may be assembled or otherwise positioned together.

Figure 9:
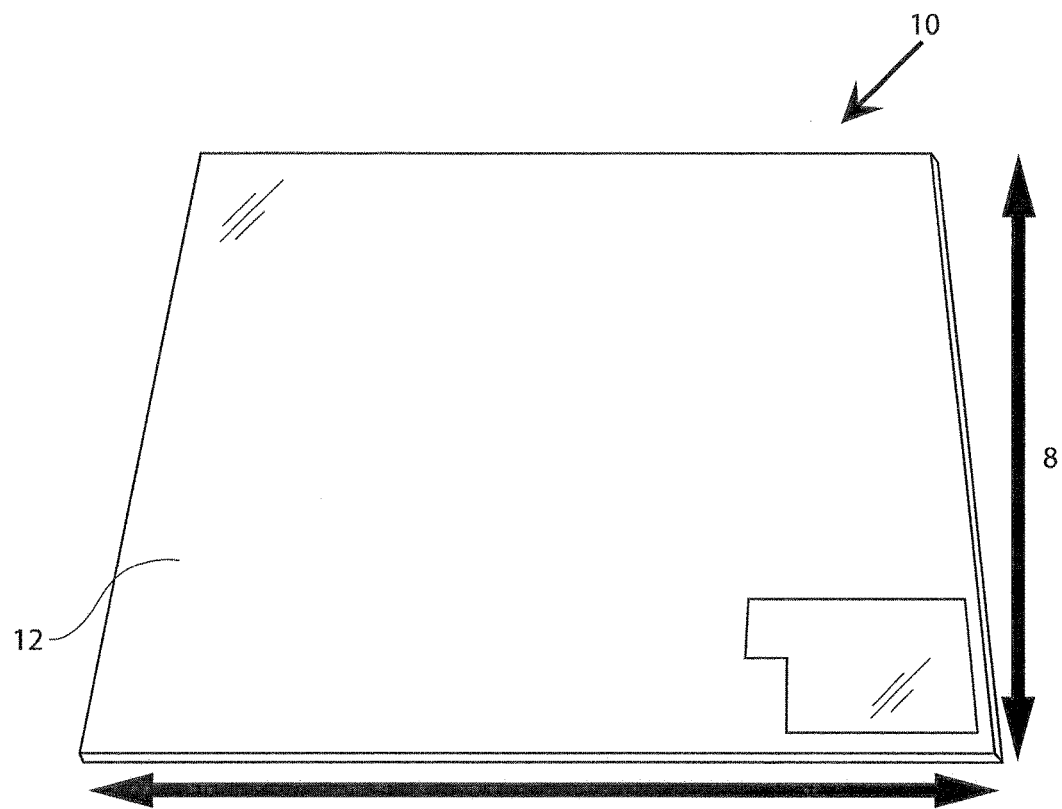
FIG. 9 shows a top view of an exemplary embodiment of a first layer of a plate reader device disclosed herein.
Figure 10:
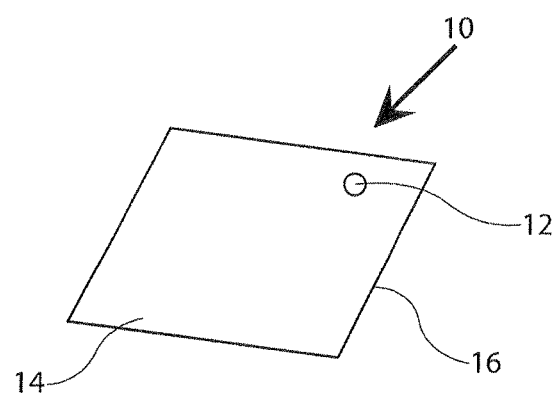
FIG. 10 shows a perspective view of an exemplary embodiment of a first layer of a plate reader device disclosed herein.

FIGS. 9-10 depict an exemplary embodiment of a first layer 10 of the device. The first layer 10 typically will comprise a flat or substantially flat piece of material. The first layer 10 may include a first surface 14 and a second surface 16 on opposing sides of the layer. Preferably, the first layer 10 will be of uniform thickness. In a preferred embodiment, the first layer may comprise a sheet of plexiglass. The first layer 10 may include one or more transparent portions 12. The one or more transparent portions 12 may be of the same or varying sizes, shapes, diameters, etc. The spacing of the transparent portions 12 may be uniform in one or more dimensions of the first layer 10. Alternatively, the transparent portions 12 may be randomly or irregularly spaced. In certain embodiments, the first layer may be entirely transparent.

Figure 11:
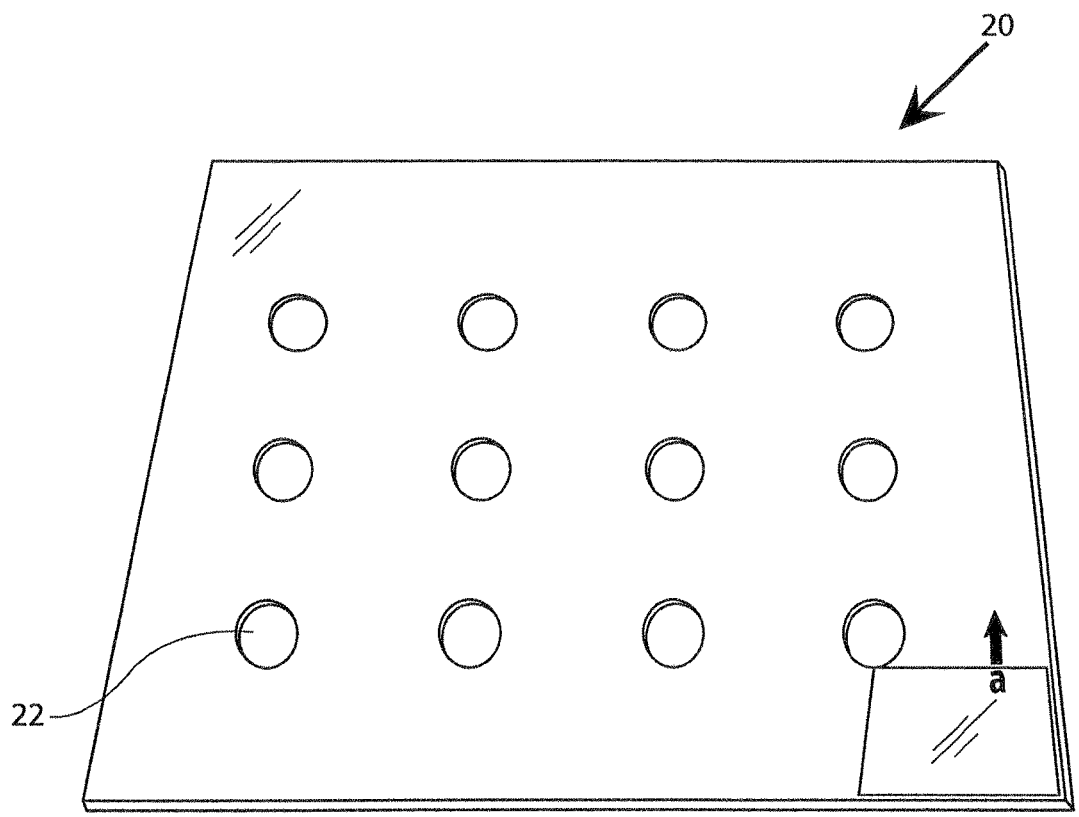
FIG. 11 shows a top view of an exemplary embodiment of a second layer of a plate reader device disclosed herein.
Figure 12:
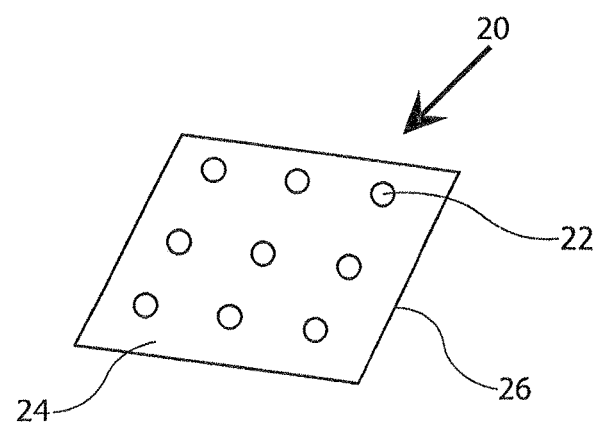
FIG. 12 shows a perspective view of an exemplary embodiment of a second layer of a plate reader device disclosed herein.

A second layer 20 of the device is shown in FIGS. 11-12. The second layer will typically comprise a flat or substantially flat piece of material. The second layer 20 may include a first surface 24 and a second surface 26 on opposing sides of the second layer. Preferably, the second layer 20 will be of substantially uniform thickness. In a preferred embodiment, the second layer 20 may comprise a sheet of plexiglass. One or more holes 22 are formed in second layer 20. The holes may extend entirely through second layer 20 (i.e., extend from a first surface 24 to a second surface 26), or alternatively may only extend partially through second layer 20. The one or more holes 22 may be of the same or varying sizes, shapes, diameters, etc. The spacing of the holes 22 may be uniform in one or more dimensions of the second layer 20. Alternatively, the holes 22 may be randomly or irregularly spaced.

Figure 16:
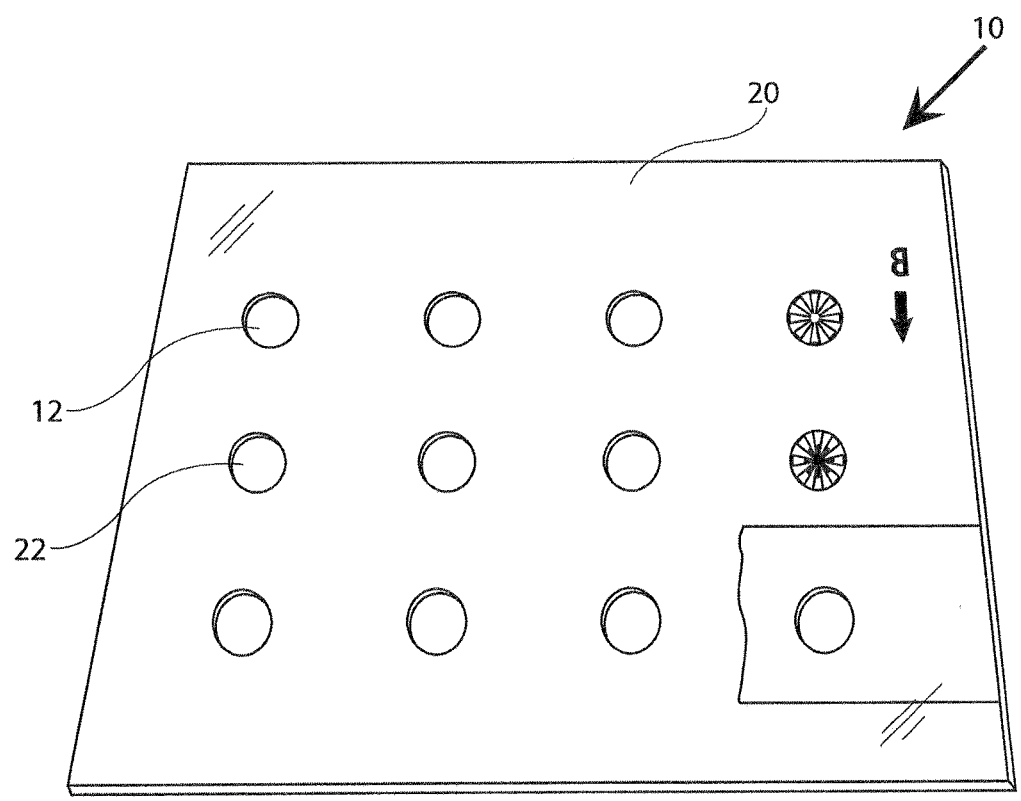
FIG. 16 shows a top view of an exemplary embodiment of an assembled first layer and second layer of a plate reader device disclosed herein.

In a preferred embodiment, the holes 22 should be sufficiently sized such that each hole may receive a dried blood sample, as is shown in FIG. 16. Typically, such a blood sample will be contained on a paper filter 28 or other similar substrate. Thus, each of the one or more holes 22 should be large enough that a filter 28 or similar substrate containing a blood sample can lay flat within the hole. In a preferred embodiment, the dimensions of the hole will closely match or be slightly larger than the dimensions of the filter or substrate such that any movement or shifting of the filter or substrate within the hole will be limited or eliminated.

Figure 13:
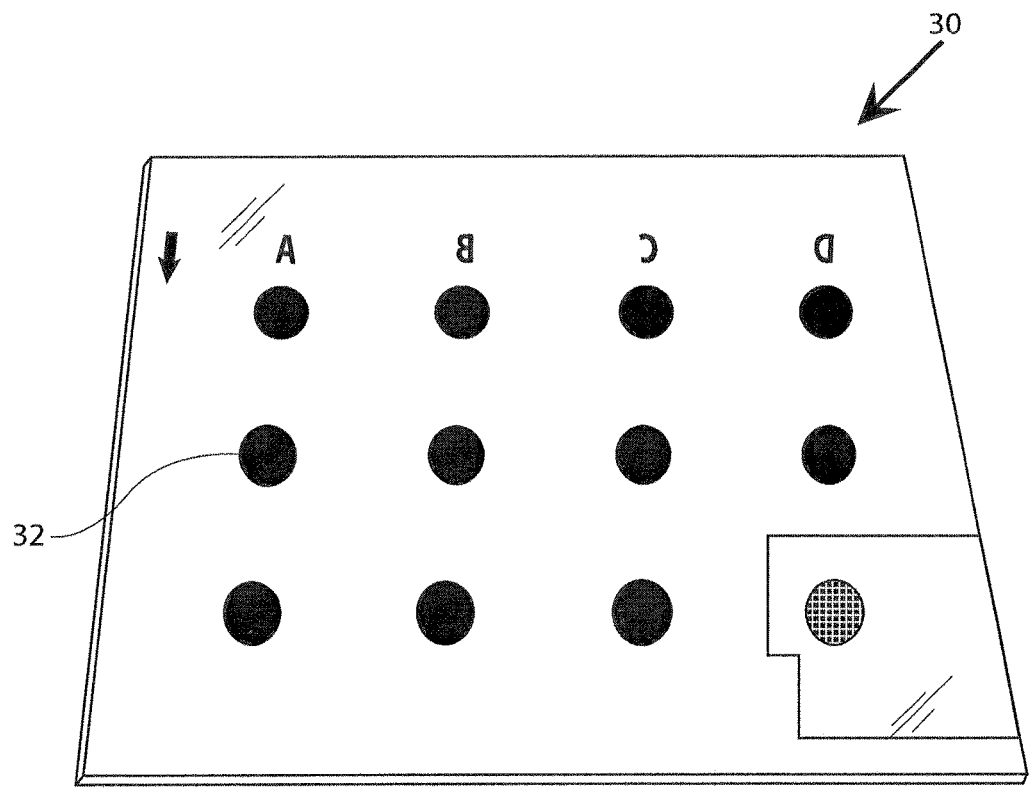
FIG. 13 shows a top view of an exemplary embodiment of a third layer of a plate reader device disclosed herein.
Figure 14:
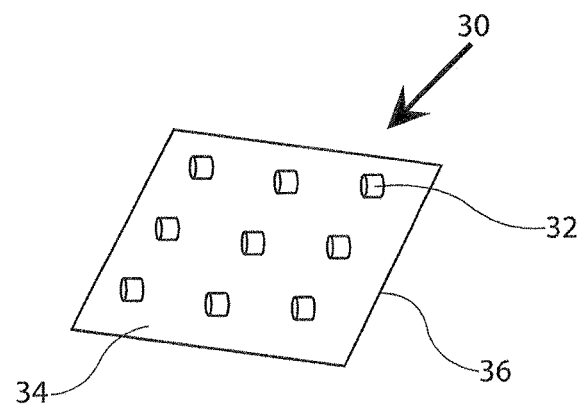
FIG. 14 shows a perspective view of an exemplary embodiment of a third layer of a plate reader device disclosed herein.

FIGS. 13-14 show a third layer 30 of the device. The third layer 30 will typically comprise a flat or substantially flat piece of material. The third layer 30 may include a first surface 34 and a second surface 36 on opposing sides of the third layer. Preferably, the third layer 30 will be of substantially uniform thickness. In a preferred embodiment, the third layer 30 may comprise a sheet of plexiglass. This layer includes one or more raised portions 32 extending upward from a first surface 34 of the third layer. The raised portions 32 may be of any size, shape or color. They may be formed integrally from the third layer 30 or may alternatively be separate components that are attached to the third layer 30 via any adhesive mechanism known in the art. The raised portions 32 may comprise any suitable material, including acrylic, plastics, metals, etc. In a preferred embodiment, the raised portions 32 may comprise acrylic discs. In a preferred embodiment, the raised portions 32 may be sized such that each raised portion fits into a hole 22 in the second layer 20 when the second and third layers are aligned and stacked on top of each other.

Figure 15:
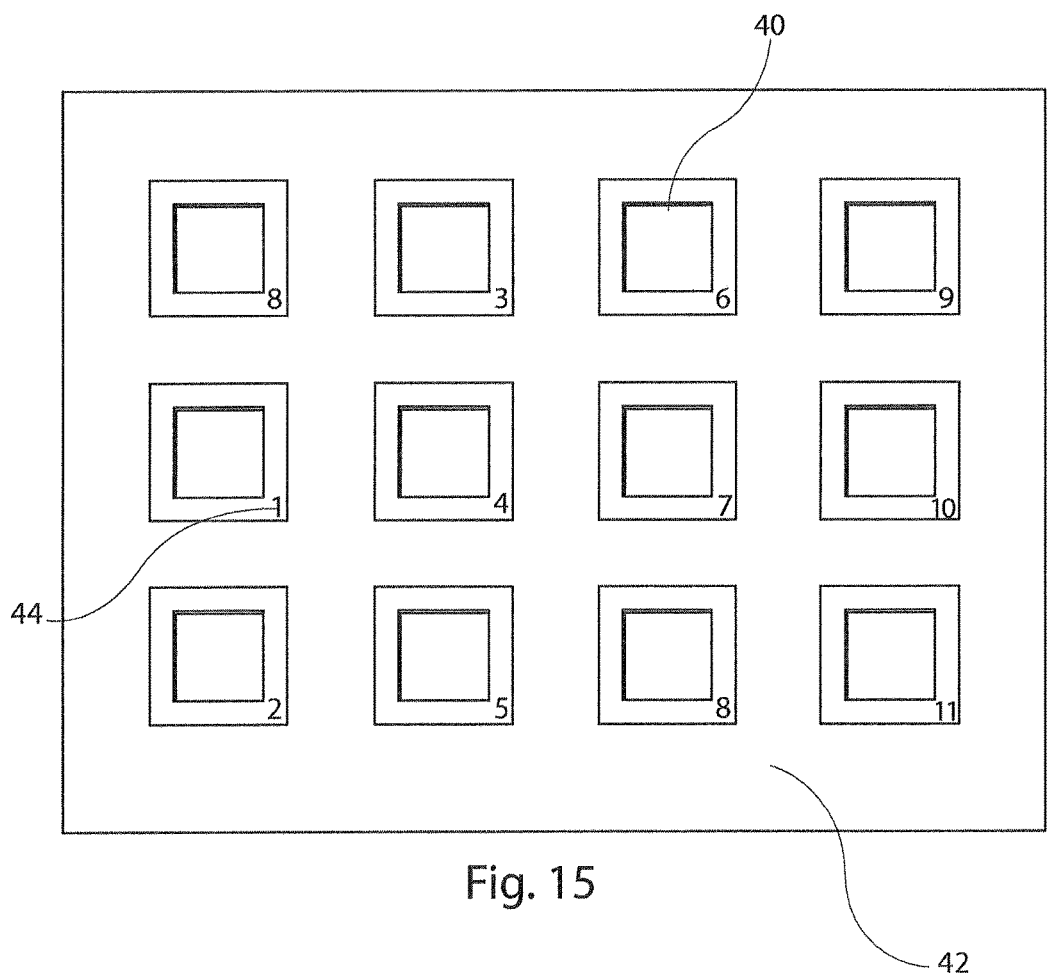
FIG. 15 shows a top view of an exemplary embodiment of labels of a plate reader device disclosed herein.

FIG. 15 shows one or more labels 40 that may be used with the device. The one or more labels may each be separate, or, alternatively may be included on a template 42 of multiple labels. In either case the labels should be removable from the device. Thus, the one or more labels, or a template containing the labels, may be configured to lie over or rest upon one or more layers of the device. Alternatively, the one or more labels, or a template containing the labels, may include an adhesive that permits both secure attachment of the labels to one or more layers of the device, as well as removal of the labels from the device. The labels and/or template containing the labels may comprise any suitable material, including paper, transfer plastic, cardboard, plexiglass, etc. The labels may comprise a code 44 for identifying a specimen (e.g., blood sample, filter, substrate, etc.) held within the device. One or more types of codes 44 may be used, including letters, words, numbers, colors, bar codes, matrix bar codes, or any combination thereof.

In a preferred embodiment, each of the first, second and third layers will comprise a substantially similar size and shape. Preferably, the layers will be sized such that they may be used in conjunction with a standard scanner or other imaging device. Thus, in certain embodiments, the layers may be substantially the same length and width as a piece of typing paper. Such a size permits the device to sit on the bed of a scanner such that any specimens within the device may be scanned. The first, second and third layers may comprise the same or different materials. Preferably, the layers will comprise plexiglass or other plastics.

Figure 17:
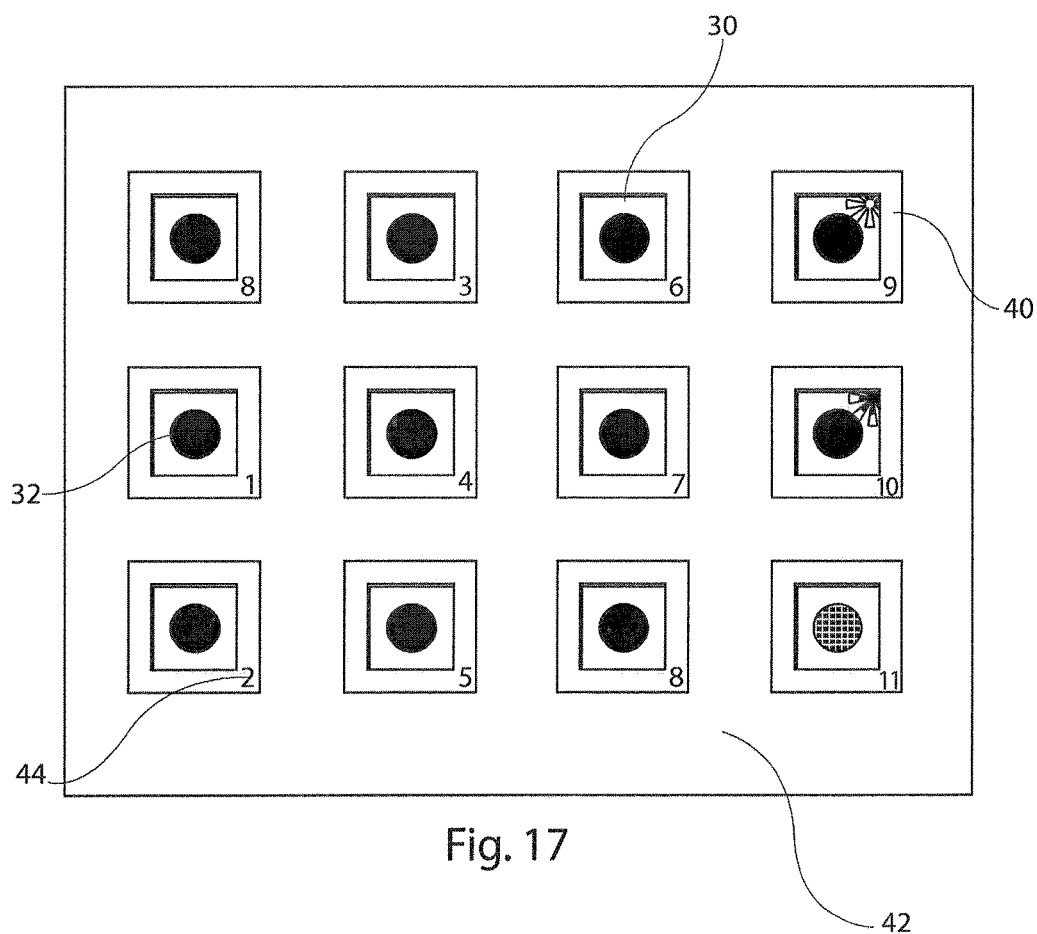
FIG. 17 shows a top view of an exemplary embodiment of an assembled third layer and labels of a plate reader device disclosed herein.
Figure 18:
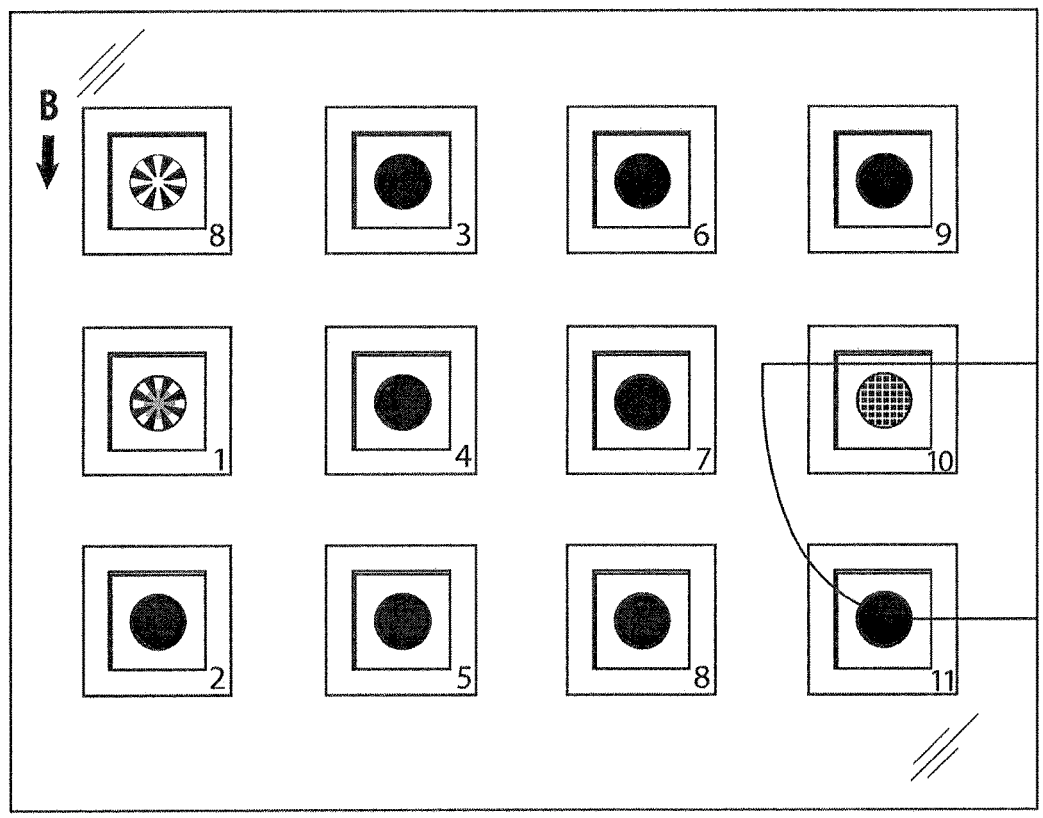
FIG. 18 shows a top view of an exemplary embodiment of an assembled plate reader device disclosed herein.

The layers, as well as the labels, are configured to be assembled together to form the device 1, as is shown in FIGS. 16-18. The layers, when assembled, may simply be aligned and stacked such that the length and width of each layer aligns or substantially aligns with the lengths and widths of the other layers. Alternatively, the layers may be securely assembled by an attachment mechanism, including screws, bolts, nails, chemical adhesives, tape, elastic bands, or combinations thereof. In one embodiment, the raised portions 32 on the third layer 30 fit tightly into the holes 22 in the second layer such that the layers are held snug. The assembly may also be securely held on the edges with tape.

When the device is assembled and all parts are aligned, the various components of each layer should also align with one another. That is, the transparent portions 12 of the first layer 10 should align with the holes 22 of the second layer 20, the raised portions 32 of the third layer 30, and the labels 40. The layers will typically be stacked with the second layer between the first and third layers. Thus, each of the one or more raised portions 32 of the third layer 30 will fit into a hole 22 of the second layer, while each one or more transparent portions 12 of the first layer will cover the holes 22 on the opposite surface of the hole from the surface where the raised portions are inserted. Further, when the device is assembled and a filter or other substrate is also inserted in a hole (as is shown in FIG. 16), the raised portions will hold the filter within the hole and compress it against a transparent portion of the first layer (as is shown in FIG. 18). Thus, the raised portions 32 preferably will extend the full depth of the hole or nearly the full depth of the hole. Further, the insertion of the raised portions in the holes also provides a secure assembly of the device by limiting relative movement of the second and third layers.

When assembled, the labels 40, or a template 42 containing the labels, will typically be attached to or otherwise lie adjacent to the third layer, as is shown in FIG. 18. However, the labels or template may also be attached, adhered, or otherwise lie adjacent to the first or second layers also.

Example 4: Exemplary Characteristics of Device Components

In an exemplary embodiment, the components of the device may have the following characteristics. The first layer comprises an 8×11" piece of plain plexiglass (FIG. 9). The second layer comprises an 8×11" piece of plain plexiglass with ¾" holes drilled into it (FIG. 11). The third layer comprises an 8×11" piece of plain plexiglass with ¾" colored acrylic discs attached to it that correspond to the ¾" holes drill in the second layer (FIG. 13). The labels are included on a removable template (comprising paper and/or transfer plastic) for labeling the samples (FIG. 15). The labels comprise a number system.

Example 5: Assembly of the Device

In an exemplary embodiment, the components of the device are assembled as follows. The first and second layers are attached together in such a way that the transparent portions of the first layer correspond with the holes in the second layer (FIG. 16). A blank piece of filter paper is placed a hole of the second layer and the remaining holes are filled with filters containing dried blood spots. The third layer and label template are assembled (FIG. 17) and placed on top of the first and second layers, such that each label corresponds to the appropriate filter or blood sample. Also, the raised portions (acrylic discs) of the third layer compress the filters down within each hole so than an accurate scan can be made of 100% of the surface area of each specimen. The whole assembled device (FIG. 18) is then placed in the scanner and scanned.

It should be emphasized that the above-described embodiments of the present disclosure, particularly, any "preferred" embodiments, are merely possible examples of implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure and the present disclosure and protected by the following claims.

What is claimed is:

1. A method for estimating the volume of a blood sample comprising the following steps:
   obtaining a fresh sample of blood;
   spotting the sample of blood on a filter paper substrate and permitting the blood sample to dry;
   obtaining an image of the dried blood spot sample;
   determining an approximate coverage or area of the image of the dried blood spot sample by counting pixels in the image of the dried blood spot sample; and
   comparing the determined approximate coverage or area of the dried blood spot sample to a standard curve to determine an estimated volume of the fresh blood spot sample.

2. The method of claim 1, further comprising calculating a coverage ratio of the dried blood spot sample on the substrate by counting pixels in an image of a blank substrate, wherein calculating the coverage ratio of the dried blood spot sample on the substrate comprises determining a ratio of the number of pixels counted in the image of the dried blood spot sample to the number of pixels counted in the image of the blank substrate.

3. The method of claim 2, wherein the standard curve comprises data from two or more fresh blood samples of known volumes plotted against data of approximate coverages or areas of the two or more fresh blood samples determined from images of the two or more fresh blood samples.

4. The method of claim 3, wherein the two or more fresh blood samples of known volumes comprise samples with varying hematocrits.

5. The method of claim 1, wherein the image of the dried blood spot sample is obtained with a scanner or a camera.

6. A device for scanning filters for dried blood samples comprising:
   a first layer comprising one or more transparent portions;
   a second layer comprising one or more holes, wherein said one or more holes are formed through the second layer and are sized to each receive a dried blood sample filter; and
   a third layer comprising one or more raised portions;
   wherein said one or more transparent portions of the first layer overlap with the one or more holes of the second layer and the one or more raised portions of the third layer when the first, second and third layers are aligned and stacked on top of each other with the second layer between the first and third layers.

7. The device of claim 6, wherein each of the one or more raised portions of the third layer fits into each of the one or more holes in the second layer.

8. The device of claim 7, wherein the raised portions of the third layer are sized to compress a dried blood spot filter against the first layer and within a hole of the second layer when the first, second and third layers are aligned and stack on top of each other with the second layer between the first and third layers.

9. The device of claim 6, wherein the first, second and third layers are configured to be securely assembled to one another such that the second layer is positioned between the first and third layers.

10. The device of claim 9, wherein the first, second, and third layers are secured by an attachment mechanism selected from the group consisting of one or more screws one or more bolts, one or more nails, a chemical adhesive, a tape, one or more elastic bands, and combinations thereof.

11. The device of claim 6, wherein at least one of the first, second or third layers comprises plexiglass.

12. The device of claim 6, wherein the first, second and third layers are substantially rectangular in shape and substantially the same size.

13. The device of claim 6, wherein the first layer is entirely transparent.

14. The device of claim 6, wherein the one or more raised portions on the third layer comprise acrylic discs.

15. The device of claim 6, further comprising one or more labels for identifying the dried blood sample filters.

16. The device of claim 15, wherein the labels comprise one or more codes comprising one or more of letters, words, numbers, colors, bar codes, and matrix bar codes.

17. The device of claim 15, wherein the one or more labels are removable.

18. The device of claim 6, wherein the one or more holes in the second layer are uniformly sized and/or uniformly spaced apart from one another.

* * * * *